(12) United States Patent
Khatibzadeh et al.

(10) Patent No.: US 12,150,900 B2
(45) Date of Patent: Nov. 26, 2024

(54) CORNEAL LENTICULAR INCISION USING A FEMTOSECOND LASER WITH OPTIMIZED PULSE ENERGY AND SCAN LINE STEPS

(71) Applicant: AMO Development, LLC, Santa Ana, CA (US)

(72) Inventors: Nima Khatibzadeh, San Jose, CA (US); Li Bing, San Jose, CA (US); Hong Fu, Pleasanton, CA (US)

(73) Assignee: AMO Development, LLC, Irvine, CA (US)

( * ) Notice: Subject to any disclaimer, the term of this patent is extended or adjusted under 35 U.S.C. 154(b) by 345 days.

(21) Appl. No.: 17/457,034

(22) Filed: Nov. 30, 2021

(65) Prior Publication Data

US 2023/0165717 A1    Jun. 1, 2023

(51) Int. Cl.
*A61F 9/008* (2006.01)
*A61B 18/20* (2006.01)

(52) U.S. Cl.
CPC ...... *A61F 9/00827* (2013.01); *A61F 9/00836* (2013.01); *A61B 2018/20353* (2017.05); *A61B 2018/20355* (2017.05); *A61F 2009/00872* (2013.01); *A61F 2009/00897* (2013.01)

(58) Field of Classification Search
CPC .......................... A61F 9/008; A61F 2009/008
See application file for complete search history.

(56) References Cited

U.S. PATENT DOCUMENTS

| 10,709,611 | B2 | 7/2020 | Fu et al. |
|---|---|---|---|
| 2016/0089270 | A1 | 3/2016 | Fu |
| 2017/0007112 | A1* | 1/2017 | Gonzalez ............. A61F 9/0084 |
| 2017/0367883 | A1 | 12/2017 | Malek Tabrizi et al. |
| 2019/0015253 | A1 | 1/2019 | Rathjen |
| 2019/0038373 | A1 | 2/2019 | Jung |
| 2019/0110926 | A1 | 4/2019 | Malek Tabrizi et al. |
| 2020/0046558 | A1* | 2/2020 | Fu ....................... A61F 9/00814 |
| 2020/0229975 | A1 | 7/2020 | Ferrari et al. |

FOREIGN PATENT DOCUMENTS

| EP | 1862154 | B1 | 3/2011 |
|---|---|---|---|
| EP | 3427706 | A1 | 1/2019 |
| KR | 101643648 | B1 | 8/2016 |
| KR | 101850767 | B1 | 4/2018 |
| WO | 2016137560 | A1 | 9/2016 |
| WO | 2017195912 | A1 | 11/2017 |

* cited by examiner

*Primary Examiner* — Lynsey C Eiseman
*Assistant Examiner* — Skylar Lindsey Christianson

(57) ABSTRACT

An ophthalmic surgical laser system and method for forming a lenticule in a subject's eye using "fast-scan-slow-sweep" scanning scheme. A high frequency scanner forms a fast scan line, which is placed tangential to a parallel of latitude of the surface of the lenticule and then then moved in a slow sweep trajectory along a meridian of longitude of the surface of the lenticule in one sweep. Multiple sweeps are performed along different meridians to form the entire lenticule surface, with the orientation of the scan line rotated between successive sweeps. To generate tissue bridge free incisions without leaving laser-induced marks in the eye, a laser pulse energy between 40 nJ to 70 nJ is used, and the sweeping speed is controlled such that the scan line step (the distance between the centers of consecutive scan lines) is between 1.7 μm and 2.3 μm.

20 Claims, 11 Drawing Sheets

CORNEAL LENTICULAR INCISION USING A FEMTOSECOND LASER WITH OPTIMIZED PULSE ENERGY AND SCAN LINE STEPS

BACKGROUND OF THE INVENTION

Field of the Invention

Embodiments of this invention relate generally to laser-assisted ophthalmic procedures, and more particularly, to systems and methods for lenticular incisions in the cornea.

Description of Related Art

Vision impairments such as myopia (near-sightedness), hyperopia and astigmatism can be corrected using eyeglasses or contact lenses. Alternatively, the cornea of the eye can be reshaped surgically to provide the needed optical correction. Eye surgery has become commonplace with some patients pursuing it as an elective procedure to avoid using contact lenses or glasses to correct refractive problems, and others pursuing it to correct adverse conditions such as cataracts. And, with recent developments in laser technology, laser surgery is becoming the technique of choice for ophthalmic procedures.

Different laser eye surgical systems use different types of laser beams for the various procedures and indications. These include, for instance, ultraviolet lasers, infrared lasers, and near-infrared, ultra-short pulsed lasers. Ultra-short pulsed lasers emit radiation with pulse durations as short as 10 femtoseconds and as long as 3 nanoseconds, and a wavelength between 300 nm and 3000 nm.

In particular, since introduction of the femtosecond lasers in ophthalmology, these lasers have been extensively used in the femtosecond laser-assisted in situ keratomileusis (FS-LASIK) refractive procedures to treat myopia and astigmatism, and in the laser-assisted cataract surgeries. Superior precision and reproducibility in performing cataract anterior capsulotomy and lens fragmentation and in the lamellar flap creation are among the main advantages of the femtosecond lasers as compared to the mechanical techniques. Short pulse duration and high repetition rate of the femtosecond lasers enable application of lower levels of energy than the ones with the picosecond and nanosecond lasers in creation of the laser-induced plasma and cavitation bubbles required for tissue photo-dissection. Lower pulse energy combined with low absorption of the laser light by tissue within near infrared wavelength range significantly reduces the thermal effects and collateral damage to the neighboring tissue in femtosecond laser-assisted ophthalmic procedures.

Prior surgical approaches for reshaping the cornea include laser assisted in situ keratomileusis (LASIK), photorefractive keratectomy (PRK) and corneal lenticule extraction.

In the LASIK procedure, an ultra-short pulsed laser is used to cut a corneal flap to expose the corneal stroma for photoablation with ultraviolet beams from an excimer laser. Photoablation of the corneal stroma reshapes the cornea and corrects the refractive condition such as myopia, hyperopia, astigmatism, and the like. In a PRK procedure where no flap is created, the epithelium layer is first removed, and some stroma material is then removed by an excimer laser. The epithelium layer will grow back within a few days after the procedure.

In a corneal lenticule extraction procedure, instead of ablating corneal tissue with an excimer laser following the creation of a corneal flap, the technique involves tissue removal with two or more femtosecond laser incisions that intersect to create a lenticule for extraction. The extraction of the lenticule changes the shape of the cornea and its optical power to accomplish vision correction. Lenticular extractions can be performed either with or without the creation of a corneal flap. With the flapless procedure, a refractive lenticule is created in the intact portion of the anterior cornea and removed through a small incision. Methods for corneal lenticule extraction using a fast-scan-slow-sweep scheme of a surgical ophthalmic laser system are described in U.S. Pat. Appl. Pub. No. 20160089270, entitled "Systems And Methods For Lenticular Laser Incision," published Mar. 31, 2016, and U.S. Pat. Appl. Pub. No. 20200046558, entitled "High Speed Corneal Lenticular Incision Using A Femtosecond Laser," published Feb. 13, 2020.

SUMMARY OF THE INVENTION

Embodiments of the present invention provide a lenticular incision method using a pulsed laser which can reduce unnecessary laser energy exposure in the center area of the patient's field of view and reduce the time required for forming the incision.

In one aspect, embodiments of the present invention provides an ophthalmic surgical laser system which includes: a laser source configured to generate a pulsed laser beam comprising a plurality of laser pulses; a laser delivery system configured to deliver the pulsed laser beam to a target tissue in a subject's eye; a high frequency scanner configured to scan the pulsed laser beam back and forth at a predefined frequency; an XY-scanner configured to deflect the pulsed laser beam, the XY-scanner being separate from the high frequency scanner; a Z-scanner configured to modify a depth of a focus of the pulsed laser beam; and a controller configured to control the laser source, the high frequency scanner, the XY-scanner and the Z-scanner to successively form a plurality of sweeps which collectively form at least one lenticular incision of a lens in the subject's eye, the lens having a curved surface that defines an apex and a Z axis passing through the apex, wherein each sweep is formed by: controlling the laser source to generate the pulsed laser beam having a pulse energy of 40 nJ to 70 nJ; controlling the high frequency scanner to deflect the pulsed laser beam to form a scan line, the scan line being a straight line having a predefined length and being tangential to a parallel of latitude of the lens, the parallel of latitude being a circle on the surface of the lens that is perpendicular to the Z axis and has a defined distance to the apex, and controlling the XY-scanner and the Z-scanner to move the scan line along a meridian of longitude of the lens, the meridian of longitude being a curve that passes through the apex and has a defined angular position around the Z axis, wherein the scan line is moved at a sweeping speed that produces a scan line step of between 1.7 μm and 2.3 μm, the scan line step being a distance between a center of consecutive scan lines; wherein the plurality of sweeps are successively formed one after another along the respective meridians of longitude which are different from one another.

In another aspect, embodiments of the present invention provide a method for creating a lenticular incision using an ophthalmic surgical laser system, the method including the steps of: generating, by a laser source, a pulsed laser beam comprising a plurality of laser pulses; delivering, by a laser delivery system, the pulsed laser beam to a target tissue in a subject's eye; scanning, by a high frequency scanner, the pulsed laser beam back and forth at a predefined frequency; deflecting, by an XY-scanner, the pulsed laser beam, the XY-scanner being separate from the high frequency scanner; modifying, by a Z-scanner, a depth of a focus of the pulsed laser beam; and controlling, by a controller, the laser source, the high frequency scanner, the XY-scanner and the Z-scanner to successively form a plurality of sweeps which collectively form at least one lenticular incision of a lens in the subject's eye, the lens having a curved surface that defines an apex and a Z axis passing through the apex, including forming each sweep by: controlling the laser source to generate the pulsed laser beam having a pulse energy of 40 nJ to 70 nJ; controlling the high frequency scanner to deflect the pulsed laser beam to form a scan line, the scan line being a straight line having a predefined length and being tangential to a parallel of latitude of the lens, the parallel of latitude being a circle on the surface of the lens that is perpendicular to the Z axis and has a defined distance to the apex, and controlling the XY-scanner and the Z-scanner to move the scan line along a meridian of longitude of the lens, the meridian of longitude being a curve that passes through the apex and has a defined angular position around the Z axis, wherein the scan line is moved at a sweeping speed that produces a scan line step of between 1.7 μm and 2.3 μm, the scan line step being a distance between a center of consecutive scan lines; wherein the plurality of sweeps are successively formed one after another along the respective meridians of longitude which are different from one another.

In yet another aspect, embodiments of the present invention provide an ophthalmic surgical laser system which includes: a laser source configured to generate a pulsed laser beam comprising a plurality of laser pulses; a laser delivery system configured to deliver the pulsed laser beam to a target tissue in a subject's eye; a high frequency scanner configured to scan the pulsed laser beam back and forth at a predefined frequency; an XY-scanner configured to deflect the pulsed laser beam, the XY-scanner being separate from the high frequency scanner; a Z-scanner configured to modify a depth of a focus of the pulsed laser beam; and a controller configured to control the laser source, the high frequency scanner, the XY-scanner and the Z-scanner to successively form a plurality of sweeps which collectively form a bed cut in the target tissue, wherein each sweep is formed by: controlling the laser source to generate the pulsed laser beam having a pulse energy of 40 nJ to 70 nJ; controlling the high frequency scanner to deflect the pulsed laser beam to form a scan line, the scan line being a straight line having a predefined length, and controlling the XY-scanner to move the scan line along a predetermined direction, wherein the scan line is moved at a sweeping speed that produces a scan line step of between 1.7 μm and 2.3 μm, the scan line step being a distance between a center of consecutive scan lines.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

DETAILED DESCRIPTION OF PREFERRED EMBODIMENTS

Embodiments of this invention are generally directed to systems and methods for laser-assisted ophthalmic procedures, and more particularly, to systems and methods for corneal lenticule incision.

Figure 1:
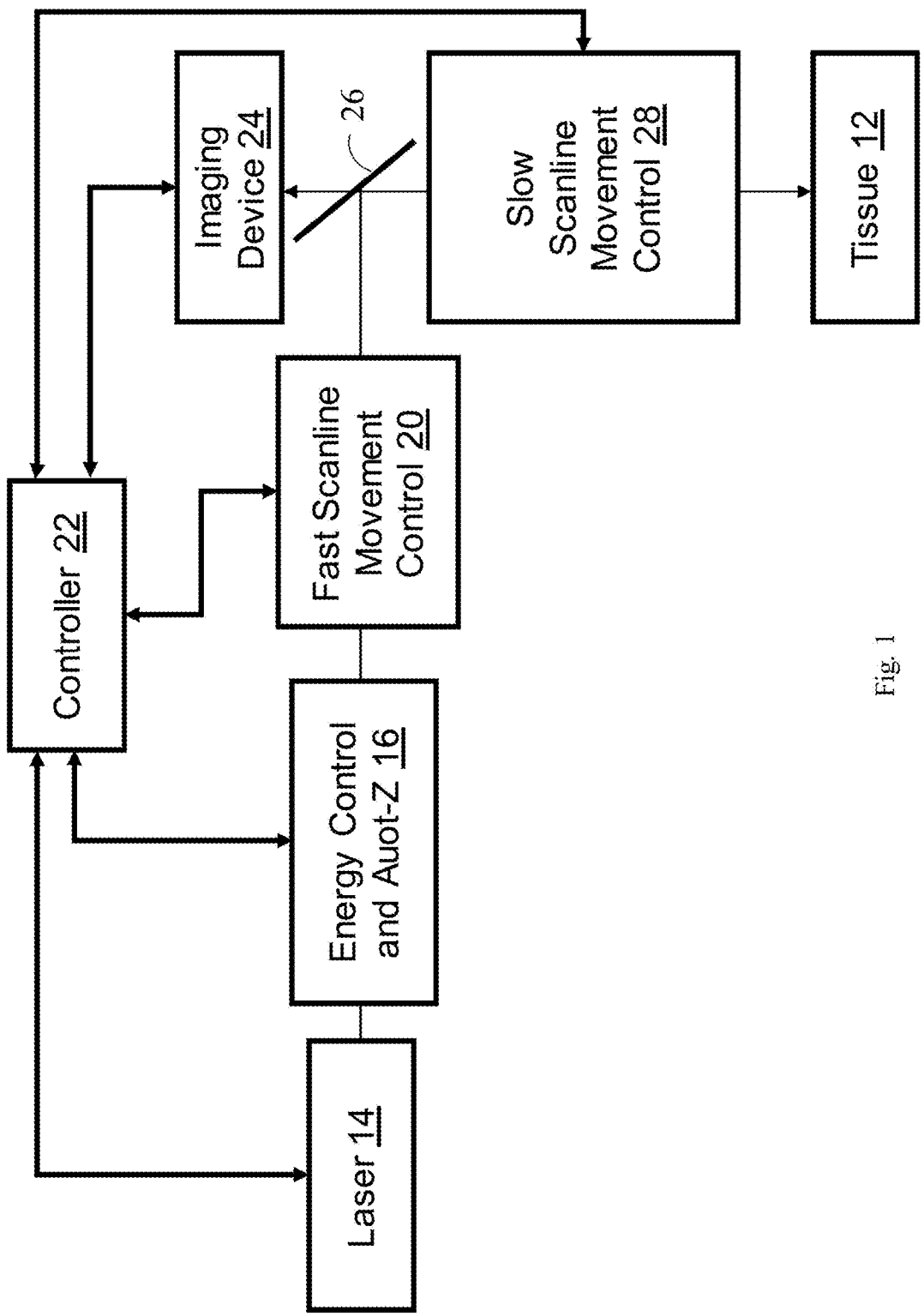
FIG. 1 is a perspective view of a surgical ophthalmic laser system which may be used to perform a lenticule incision method according to an embodiment of the present invention.

Referring to the drawings, FIG. 1 shows a system 10 for making an incision in a tissue 12 of a patient's eye. The system 10 includes, but is not limited to, a laser 14 capable of generating a pulsed laser beam, an energy control module 16 for varying the pulse energy of the pulsed laser beam, a fast scanline movement control module 20 for generating a fast scanline of the pulsed laser beam (described in more detail later), a controller 22, and a slow scanline movement control module 28 for moving the laser scanline and delivering it to the tissue 12. The controller 22, such as a processor operating suitable control software, is operatively coupled with the fast scanline movement control module 20, the slow scanline movement control module 28, and the energy control module 16 to direct the scanline of the pulsed laser beam along a scan pattern on or in the tissue 12. In this embodiment, the system 10 further includes a beam splitter 26 and a imaging device 24 coupled to the controller 22 for a feedback control mechanism (not shown) of the pulsed laser beam. Other feedback methods may also be used. In an embodiment, the pattern of pulses may be summarized in machine readable data of tangible storage media in the form of a treatment table. The treatment table may be adjusted according to feedback input into the controller 22 from an automated image analysis system in response to feedback data provided from a monitoring system feedback system (not shown).

Laser 14 may comprise a femtosecond laser capable of providing pulsed laser beams, which may be used in optical procedures, such as localized photodisruption (e.g., laser induced optical breakdown). Localized photodisruptions can be placed at or below the surface of the tissue or other material to produce high-precision material processing. For example, a micro-optics scanning system may be used to scan the pulsed laser beam to produce an incision in the material, create a flap of the material, create a pocket within the material, form removable structures of the material, and the like. The term "scan" or "scanning" refers to the movement of the focal point of the pulsed laser beam along a desired path or in a desired pattern.

In other embodiments, the laser 14 may comprise a laser source configured to deliver an ultraviolet laser beam comprising a plurality of ultraviolet laser pulses capable of photodecomposing one or more intraocular targets within the eye.

Although the laser system 10 may be used to photoalter a variety of materials (e.g., organic, inorganic, or a combination thereof), the laser system 10 is suitable for ophthalmic applications in some embodiments. In these cases, the focusing optics direct the pulsed laser beam toward an eye (for example, onto or into a cornea) for plasma mediated (for example, non-UV) photoablation of superficial tissue, or into the stroma of the cornea for intrastromal photodisruption of tissue. In these embodiments, the surgical laser system 10 may also include a lens to change the shape (for example, flatten or curve) of the cornea prior to scanning the pulsed laser beam toward the eye.

Figure 2:
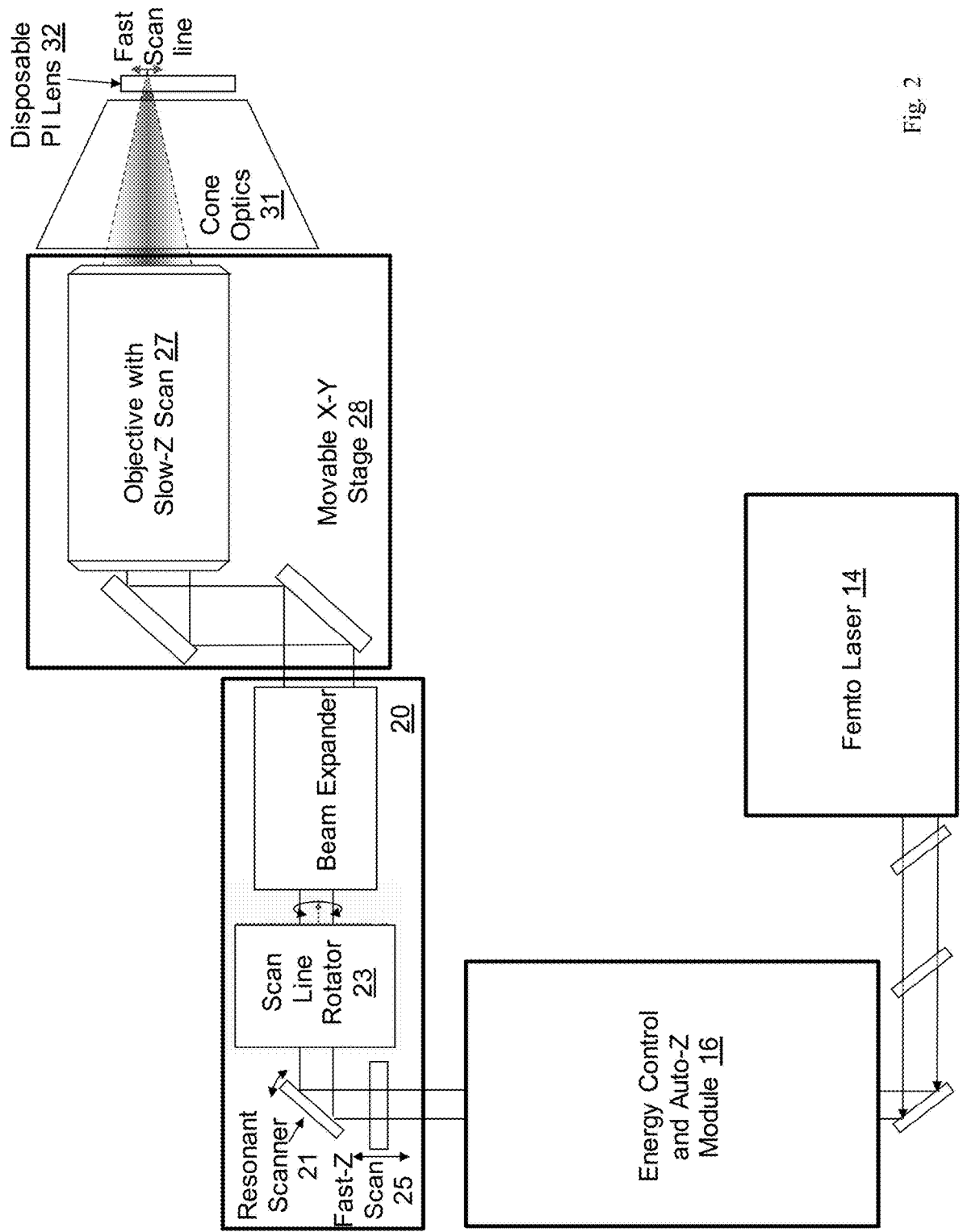
FIG. 2 is another perspective view of a surgical ophthalmic laser system which may be used to perform a lenticule incision method according to an embodiment of the present invention.

FIG. 2 shows another exemplary diagram of the laser system 10. FIG. 2 shows components of a laser delivery system including a moveable XY-scanner (or movable XY-stage) 28 of a miniaturized femtosecond laser system. In this embodiment, the system 10 uses a femtosecond oscillator, or a fiber oscillator-based low energy laser. This allows the laser to be made much smaller. The laser-tissue interaction is in the low-density-plasma mode. An exemplary set of laser parameters for such lasers include pulse energy in the 40-100 nJ range and pulse repetitive rates (or "rep rates") in the 2-40 MHz range. A fast-Z scanner 25 and a resonant scanner 21 direct the laser beam to a scanline rotator 23. When used in an ophthalmic procedure, the system 10 also includes a patient interface design that has a fixed cone nose 31 and a contact lens 32 that engages with the patient's eye. A beam splitter may be placed inside the cone 31 of the patient interface to allow the whole eye to be imaged via visualization optics. In some embodiments, the system 10 may use: optics with a 0.6 numerical aperture (NA) which would produce 1.1 μm Full Width at Half Maximum (FWHM) focus spot size; and a resonant scanner 21 that produces 0.2-1.2 mm scan line with the XY-scanner scanning the resonant scan line to a 1.0 mm field. The prism 23 (e.g., a Dove or Pechan prism, or the like) rotates the resonant scan line in any direction on the XY plane. The fast-Z scanner 25 sets the incision depth. The slow scanline movement control module employs a movable XY-stage 28 carrying an objective lens with Z-scanning capability 27, referred to as slow-Z scanner because it is slower than the fast-Z scanner 25. The movable XY-stage 28 moves the objective lens to achieve scanning of the laser scanline in the X and Y directions. The objective lens changes the depth of the laser scanline in the tissue. The energy control and auto-Z module 16 may include appropriate components to control the laser pulse energy, including attenuators, etc. It may also include an auto-Z module which employs a confocal or non-confocal imaging system to provide a depth reference. The miniaturized femtosecond laser system 10 may be a desktop system so that the patient sits upright while being under treatment. This eliminates the need of certain opto-mechanical arm mechanism(s), and greatly reduces the complexity, size, and weight of the laser system. Alternatively, the miniaturized laser system may be designed as a conventional femtosecond laser system, where the patient is treated while lying down.

Figure 3:
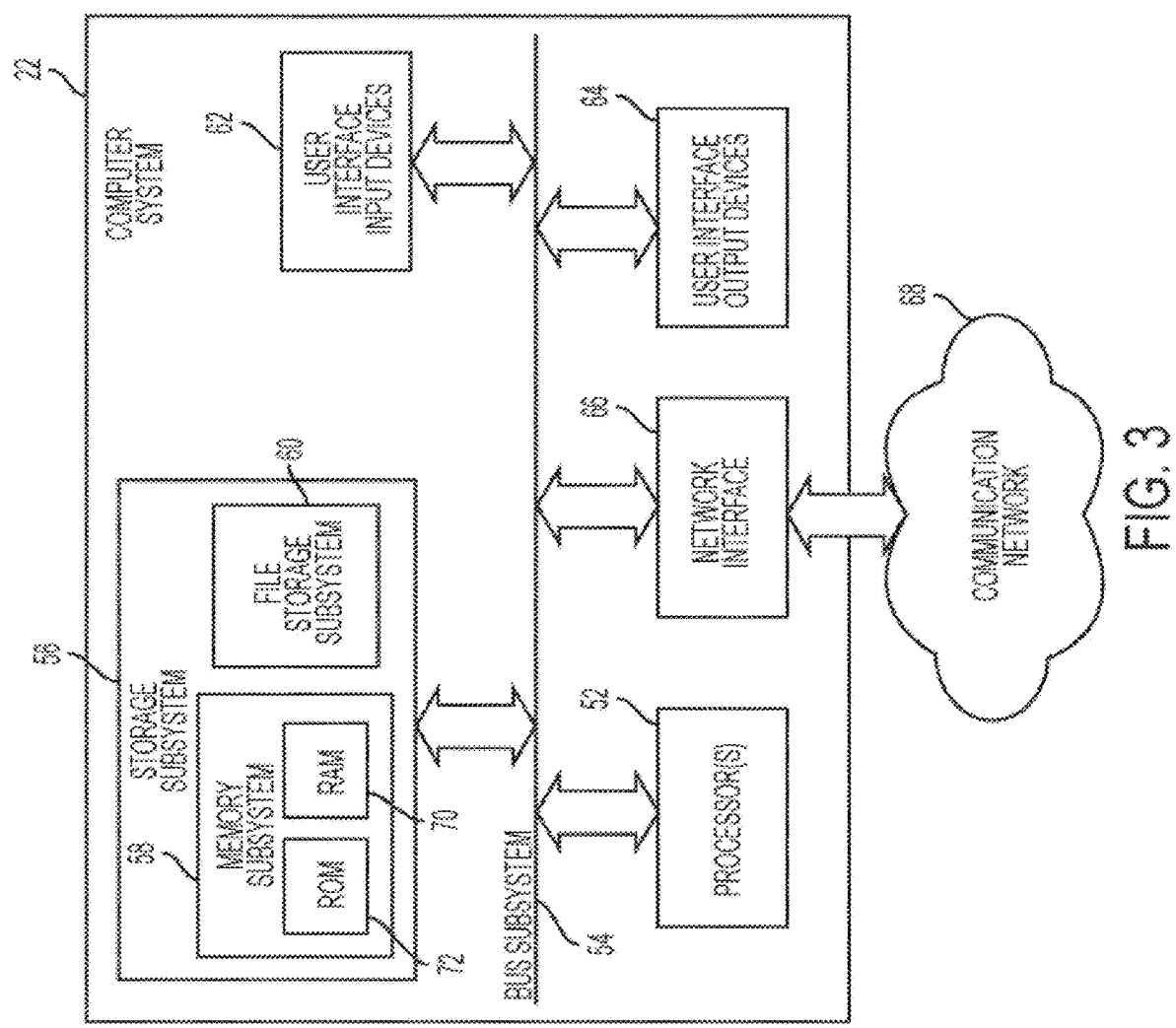
FIG. 3 is a simplified diagram of a controller of a surgical ophthalmic laser system which may be used to perform a lenticule incision method according to an embodiment of the present invention.

FIG. 3 illustrates a simplified block diagram of an exemplary controller 22 that may be used by the laser system 10 according to an embodiment of this invention to control the laser system 10 and execute at least some of the steps discussed in detail below. Controller 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices. Network interface subsystem 66 includes one or more interfaces known in the arts, such as LAN, WLAN, Bluetooth, other wire and wireless interfaces, and so on.

User interface input devices 62 may include a keyboard, pointing devices such as a mouse, trackball, touch pad, or graphics tablet, a scanner, foot pedals, a joystick, a touch screen incorporated into a display, audio input devices such as voice recognition systems, microphones, and other types of input devices. In general, the term "input device" is intended to include a variety of conventional and proprietary devices and ways to input information into controller 22.

User interface output devices 64 may include a display subsystem, a printer, a fax machine, or non-visual displays such as audio output devices. The display subsystem may be a flat-panel device such as a liquid crystal display (LCD), a light emitting diode (LED) display, a touchscreen display, or the like. The display subsystem may also provide a non-visual display such as via audio output devices. In general, the term "output device" is intended to include a variety of conventional and proprietary devices and ways to output information from controller 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files. File storage subsystem 60 may include a hard disk drive along with associated removable media, a Compact Disk (CD) drive, an optical drive, DVD, solid-state memory, and/or other removable media. One or more of the drives may be located at remote locations on other connected computers at other sites coupled to controller 22. The modules implementing the functionality of the present invention may be stored by file storage subsystem 60.

Bus subsystem 54 provides a mechanism for letting the various components and subsystems of controller 22 communicate with each other as intended. The various subsystems and components of controller 22 need not be at the same physical location but may be distributed at various locations within a distributed network. Although bus subsystem 54 is shown schematically as a single bus, alternate embodiments of the bus subsystem may utilize multiple busses.

Due to the ever-changing nature of computers and networks, the description of controller 22 depicted in FIG. 3 is intended only as an example for purposes of illustrating only one embodiment of the present invention. Many other configurations of controller 22, having more or fewer components than those depicted in FIG. 3, are possible.

As should be understood by those of skill in the art, additional components and subsystems may be included with laser system 10. For example, spatial and/or temporal integrators may be included to control the distribution of energy within the laser beam. Ablation effluent evacuators/filters, aspirators, and other ancillary components of the surgical laser system are known in the art, and may be included in the system. In addition, an imaging device or system may be used to guide the laser beam.

Figure 4:
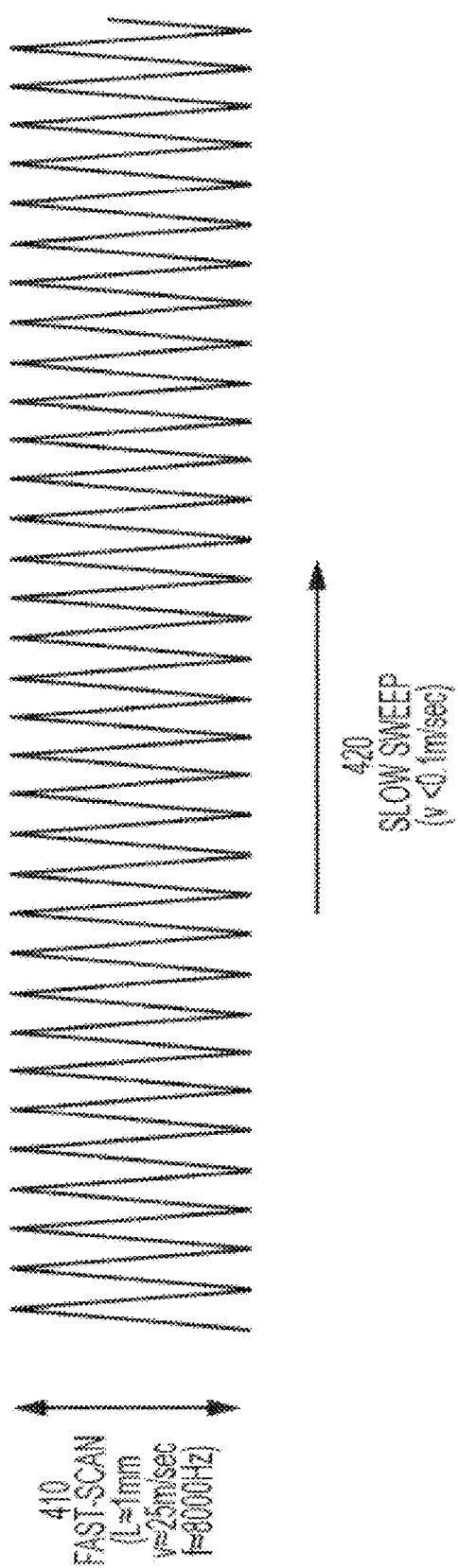
FIG. 4 illustrates an exemplary scanning of a surgical ophthalmic laser system according to an embodiment of the present invention.

In preferred embodiments, the beam scanning can be realized with a "fast-scan-slow-sweep" scanning scheme, also referred herein as a fast-scan line scheme. The scheme consists of two scanning mechanisms: first, a high frequency fast scanner is used to scan the beam back and forth to produce a short, fast scan line (e.g., a resonant scanner 21 of FIG. 2); second, the fast scan line is slowly swept by much slower X, Y, and Z scan mechanisms (e.g. the moveable X-Y stage 28 and the objective lens with slow-Z scan 27, and the fast-Z scanner 25). FIG. 4 illustrates a scanning example of a laser system 10 using an 8 kHz (e.g. between 7 kHz and 9 kHz, or more generally, between 0.5 kHz and 20 kHz) resonant scanner 21 to produce a fast scan line 410 of about 1 mm (e.g., between 0.9 mm and 1.1 mm, or more generally, between 0.2 mm and 1.2 mm) and a scan speed of about 25 m/sec, and X, Y, and Z scan mechanisms with the scan speed (sweeping speed) smaller than about 0.1 m/sec. The fast scan line 410 may be perpendicular to the optical beam propagation direction, i.e., it is always parallel to the XY plane. The trajectory of the slow sweep 420 can be any three dimensional curve drawn by the X, Y, and Z scanning devices (e.g., XY-scanner 28 and fast-Z scanner 25). An advantage of the "fast-scan-slow-sweep" scanning scheme is that it only uses small field optics (e.g., a field diameter of 1.5 mm) which can achieve high focus quality at relatively low cost. The large surgical field (e.g., a field diameter of 10 mm or greater) is achieved with the XY-scanner, which may be unlimited.

Figure 5:
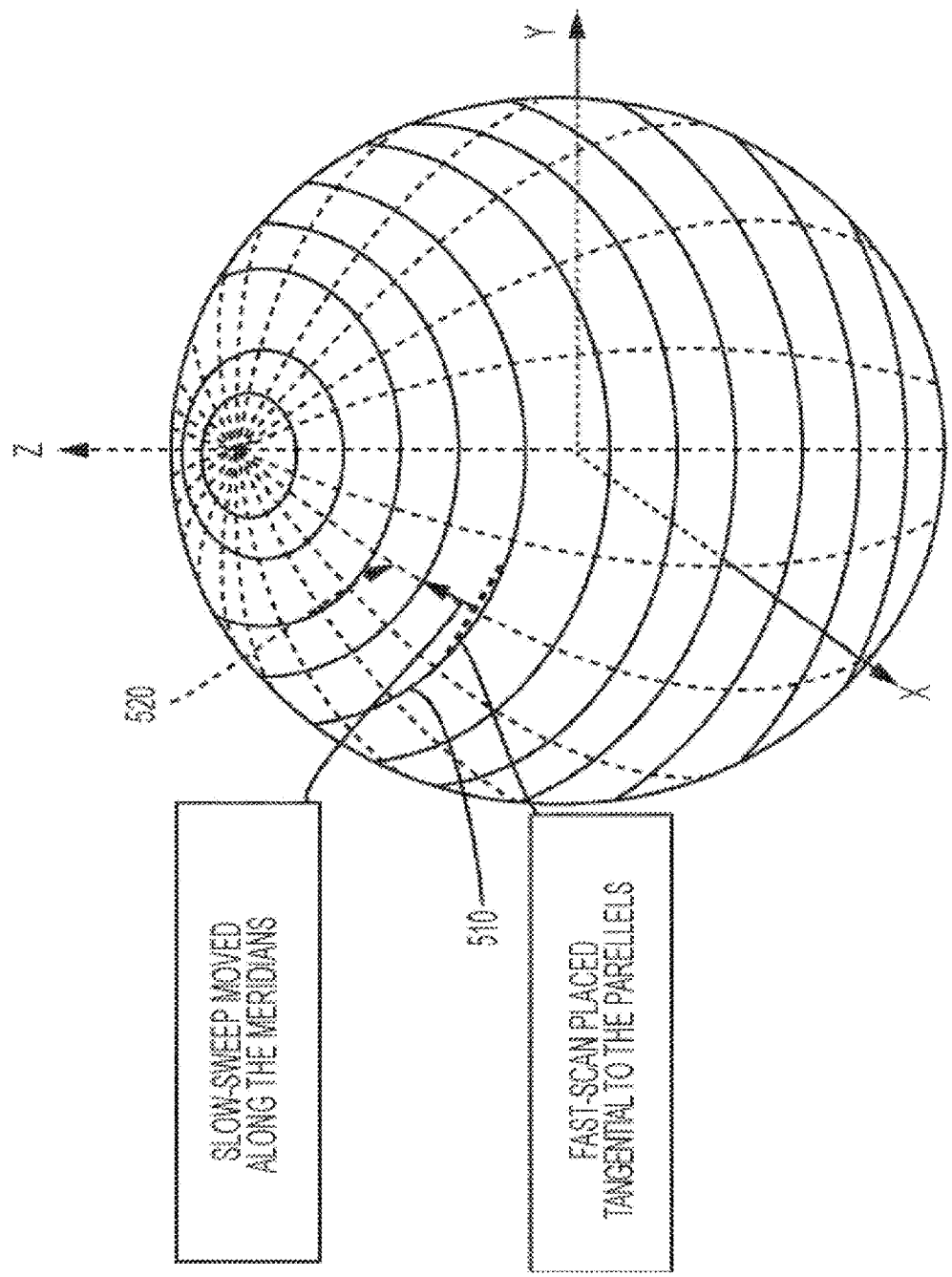
FIG. 5 illustrates an exemplary surface dissection using a fast-scan-slow-sweep scheme of a surgical ophthalmic laser system according to an embodiment of the present invention.

In a preferred embodiment shown in FIGS. 5 and 7A-7B, the laser system 10 creates a smooth lenticular cut using the "fast-scan-slow-sweep" scanning scheme under a preferred procedure. First, in a three dimensional lenticular cut, the fast scan line is preferably placed tangential to the parallels of latitude 510 on the surface of the lenticule. A parallel of latitude is the intersection of the surface with a plane perpendicular to the Z axis (which is the axis parallel to the depth direction of the eye), i.e. a circle on the surface of the lens that is perpendicular to the Z axis and has a defined distance to the apex (the highest point in the Z direction). For example, in the laser system 10 of FIG. 2, this can be realized by adjusting a prism 23 to the corresponding orientations via software, e.g., via the controller 22. Second, the slow sweep trajectory preferably moves along the meridians of longitude 520 on the surface of the lenticule. A meridian of longitude is the intersection of the surface with a plane that passes through the Z axis, i.e. a curve that passes through the apex and has a defined angular direction with respect to the Z axis. For example, in the laser system of FIG. 2, this can be done by coordinating the XY scanner 28, and the Fast-Z scanner 25 via the software, e.g., via the controller 22. The procedure starts with the scan line being parallel to the XY plane, and sweeps through the apex of the lens, following the curvature with the largest diameter (see also FIG. 7A). Multiple sweeps are performed at successive angular directions with respect to the Z axis, for example as realized by rotating the prism 23 between successive sweeps, to form the entire lenticule. With this preferred procedure, there are no vertical "steps" in the dissection, and vertical side cuts are eliminated. As will be analyzed herein below, the deviations between the laser focus locations and the intended spherical surface dissections are also minimized.

Figure 6:
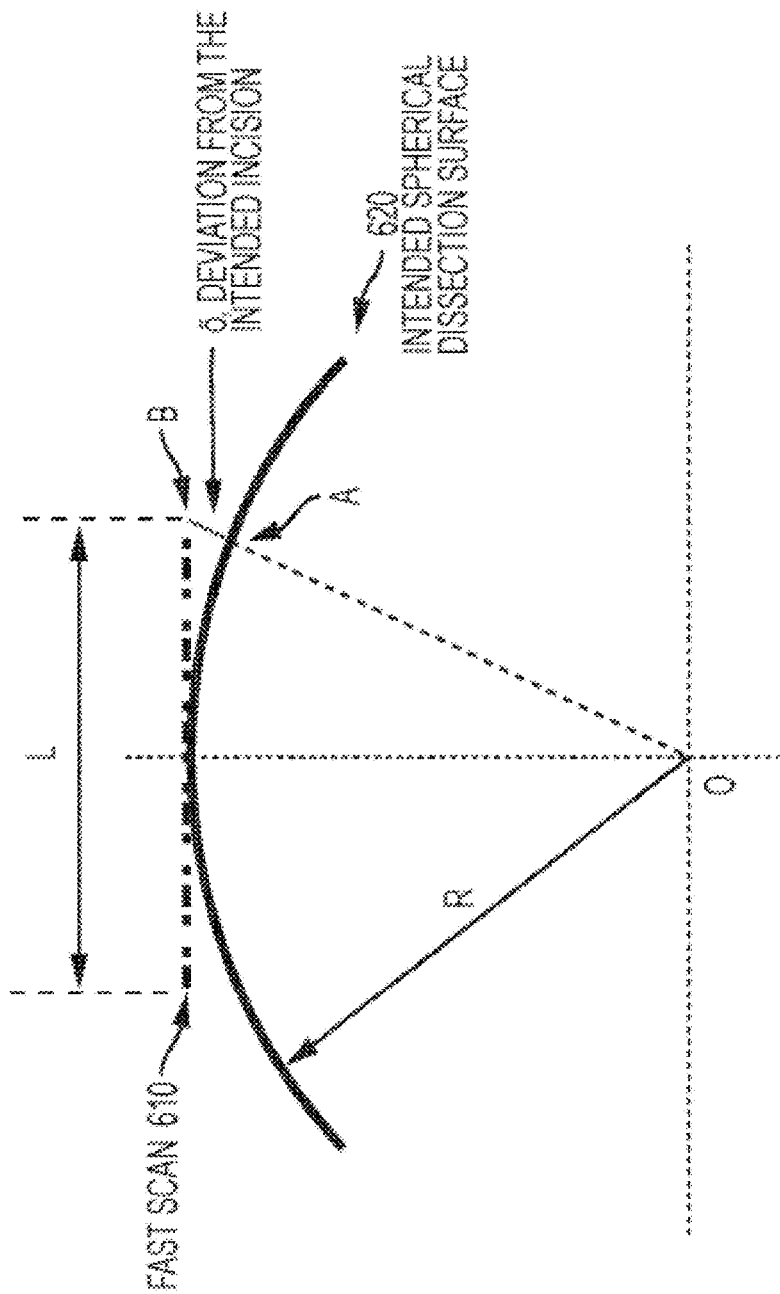
FIG. 6 illustrates a geometric relation between a fast-scan line and an intended spherical dissection surface of a surgical ophthalmic laser system according to an embodiment of the present invention.

FIG. 6 shows the geometric relation between the fast scan line 610 and the intended spherical dissection surface 620, e.g., of a lens, especially the distance deviation (δ) between the end point B of the scan line 610 and point A on the intended dissection surface 620. The maximum deviation δ is the distance between point A and point B, and is given by (Equation (1)):

$$\delta = \sqrt{R^2 + \frac{L^2}{4}} - R \approx \frac{L^2}{8R}$$

where R is greater than L. R is the radius of curvature of the surface dissection 620, and L is the length of the fast scan.

While the above maximum deviation analysis is for a spherical surface, this scanning method may also be used to create a smooth cut having a non-spherical shape, such as an ellipsoidal shape, etc. In such a case, the parallel of latitude and/or the meridian of longitude may not be circular.

In an exemplary case of myopic correction, the radius of curvature of the surface dissection may be determined by the amount of correction, ΔD, using the following equation (Equation (2)):

$$\Delta D = \frac{(n-1)}{R_1} + \frac{(n-1)}{R_2}$$

where n=1.376, which is the refractive index of cornea, and $R_1$ and $R_2$ (may also be referred herein as $R_t$ and $R_b$) are the radii of curvature for the top surface and bottom surface of a lenticular incision, respectively. For a lenticular incision with $R_1=R_2=R$ (the two dissection surface are equal for them to physically match and be in contact), we have (Equation (3)):

$$R = \frac{2(n-1)}{\Delta D}$$

Figure 7:
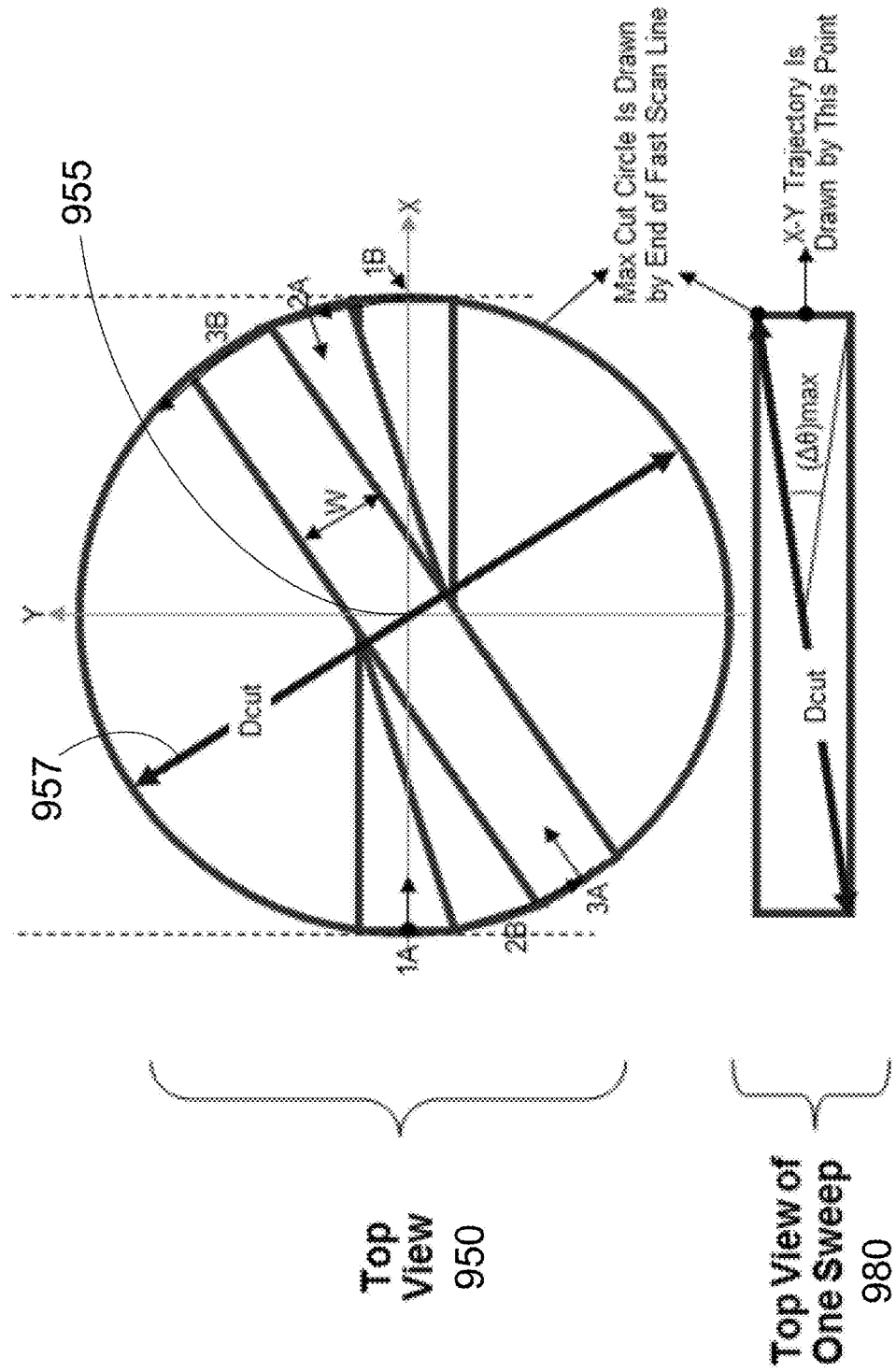
FIG. 7 illustrates an exemplary lenticular incision using a surgical ophthalmic laser system according to an embodiment of the present invention.

FIG. 7 is a top view 950 of a lenticular incision 900 which illustrates three exemplary sweeps (1A to 1B), (2A to 2B) and (3A to 3B), with each sweep going through (i.e., going over) the lenticular incision apex 955. The incision diameter 957 ($D_{CUT}$) should be equal to or greater than the to-be-extracted lenticular incision diameter. A top view 980 shows the top view of one exemplary sweep. In one example, the successive sweeps are performed at about 9° angular (rotational) increments.

To summarize, using such a "fast-scan-slow-sweep" scanning scheme, each sweep of the fast scan line forms a bent band, the bent band being the equivalent of bending a flat rectangle such that its long sides form arched shapes (the shape of the meridian of longitude) while its short sides remain straight. In the top view in FIG. 7, the rectangular shapes represent the sweeps.

In a corneal lenticule extraction clinical trial in human eyes, where the lenticule (or lens) surfaces were incised using the "fast-scan-slow-sweep" scanning scheme, some periodic radial marks were observed around the edges of the lenticular cuts in the eyes during post-surgery slit lamp examination. These marks, referred to as "spoke wheel" marks in this disclosure due to their near-radial appearance, persisted for a few months after laser surgery. Through investigation, the inventors of the present invention determined that the primary contributing factor for the residual spoke wheel marks in the cornea was the energy density (energy per unit area) of the laser pulses in the tissue, and established preferred laser system settings that achieved tissue bridge-free lenticular incisions while eliminating the spoke-wheel laser marks.

Figure 8:
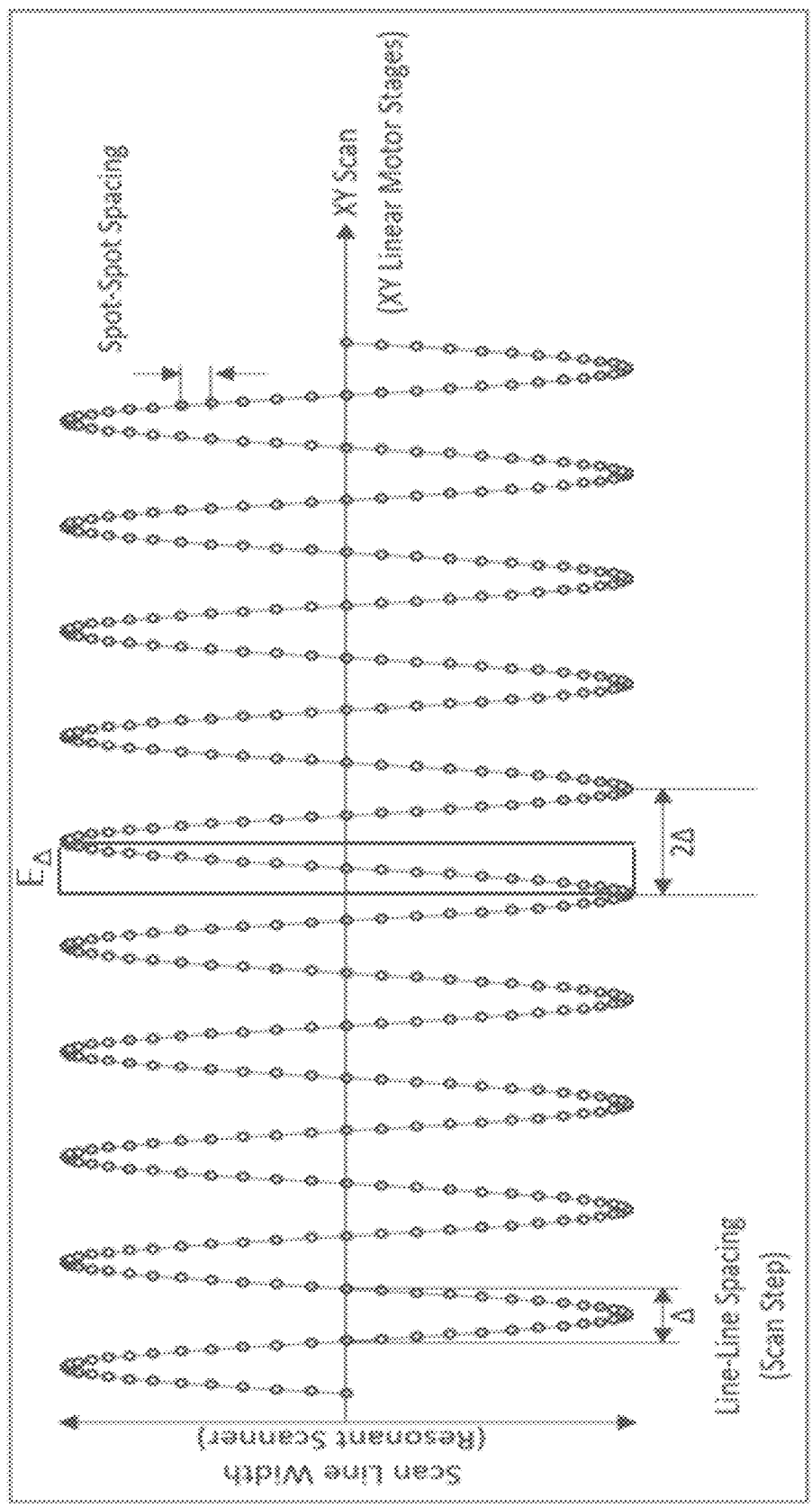
FIG. 8 schematically illustrates a wave pattern of laser focal spots formed by sweeping a laser scan line.

The inventors believe that the spoke wheel marks were caused by the relatively high energy density at the two edges of the sweeps. As schematically illustrated in FIG. 8, each scan line is a line of laser focal spots over the scan line width (e.g. 900 µm), formed by scanning the pulsed laser beam using the resonant scanner, for example, at a frequency of approximately 8 KHz (e.g., 7.9 KHz). As the scan line is swept along the meridian, the laser focal spots form a wave pattern as schematically illustrated in FIG. 8. Towards the two ends of each scan line (i.e. the two parallel edges of the sweep), the velocity of the resonant scanner decreases to zero, causing the spot-to-spot distance to decrease and the spot density to increase near the edges of the sweep. In other words, there is an accumulation of laser spots near the edges of the laser scan line. Thus, the local energy density is higher near the two edges than at the center of the sweep. This higher energy density near the edges is believed to have caused the observed spoke wheel marks.

The laser system settings used in the clinical trial were as follows. The wavelength of the femtosecond laser was 1030 nm. The duration of the laser pulse was less than 200 fs at the laser focal spot. The diameter of the laser focal spot in the cornea tissue was under 1.3 µm to achieve desired thin lenticular incision interface. The laser pulse energy values, as delivered to the tissue under treatment, were between 50 nJ and 70 nJ to prevent formation of large cavitation bubbles. More specifically, the laser pulse energy was 70 nJ for the top (anterior) lenticular incision and 60 nJ for the bottom (posterior) lenticule incision. The laser repetition rate was 10 MHz and the resonant scanner frequency was 7.9 KHz, giving 632 laser focal spots in each scan line. The scan line width was 900 µm, and the scanning speed along the scan line was about 15 m/s at the center of the scan line. Here, note that the average distance between the laser spots is generally adjustable by changing the scan line width, preferably within the range of 400 µm-900 µm, while keeping the number of laser spots in each scan line constant, such as 632 spots per line. In an actual lenticule incision, due to overlapping of adjacent sweeps, the average distance between the laser spots is approximately 1 µm.

Figure 9A:
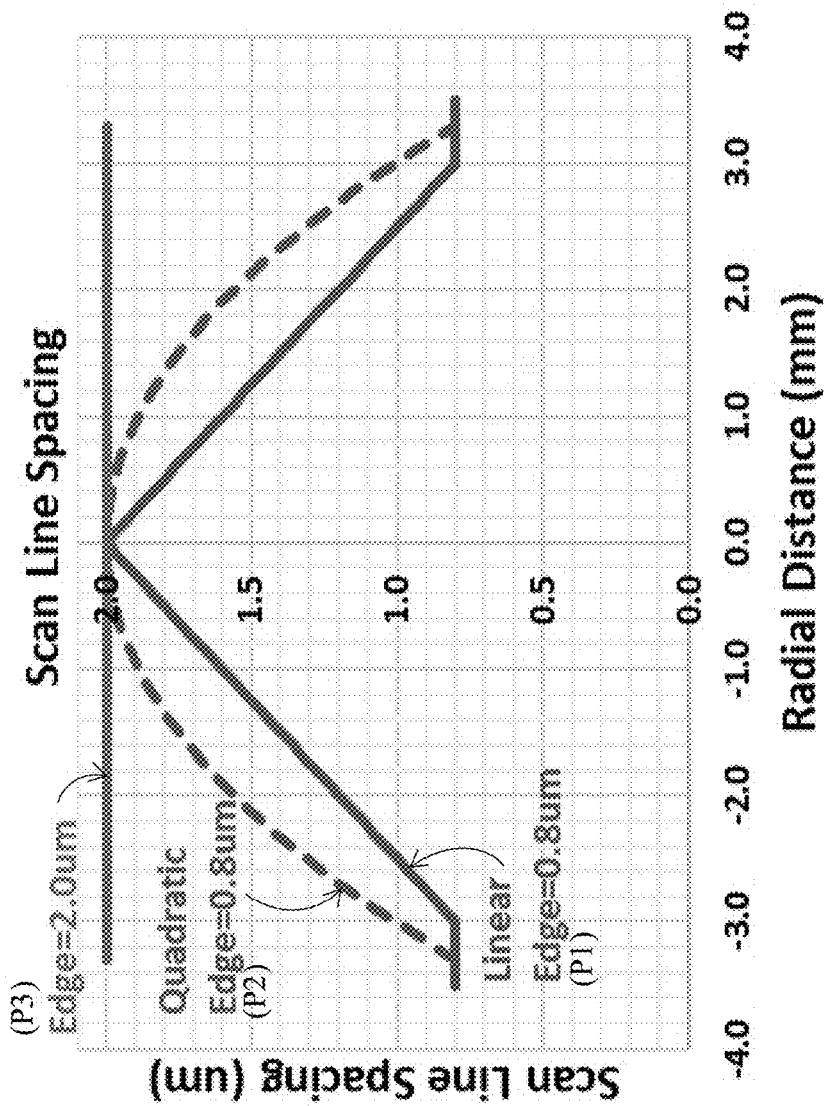
FIG. 9A schematically illustrates the scan line step as a function of radial distance from the lenticule center for three examples including an embodiment of the present invention.

The sweeping speed along the meridian was a variable speed, higher at the lenticule center (the apex) and lower at the lenticule edges: the scan line step Δ varied from 0.8 µm at the edges of the lenticule to 2.0 µm at the center of the lenticule in a linear profile, except for a peripheral ring portion, which is constant, as shown in line P1 in FIG. 9A. In this disclosure, the scan line step Δ, i.e., the distance between the center of two consecutive laser scan lines (see FIG. 8), is used as a proxy for the sweeping speed.

These settings allowed for smooth and tissue bridge-free corneal lenticule incisions; however, as mentioned earlier, a radial "spoke wheel" type of laser-induced marks were generated within the cornea.

To reduce or eliminate the spoke wheel marks, the inventors believed that the energy density (the amount of laser energy deposited into the tissue per unit tissue area) of the sweeps should be decreased. For a sweep pattern such as that shown in FIG. 8, the average energy density $E_A$ can be calculated as $E_A=n*E/(W*\Delta)$, i.e., the total energy in one scan line divided by the area spanned by one scan line, where n is the number of pulses per scan line, E is the pulse energy (energy per laser pulse), W is the scan line width, and Δ is the scan line step (see FIG. 8).

To investigate the effect of reduced energy density, a set of lenticule cutting experiments were conducted using ex vivo porcine eyes with reduced laser pulse energy, while holding the other parameters the same as in the above-mentioned clinical trial. The residual stromal bed and lenticule surfaces were inspected for surface smoothness, irregularity, and residual laser marks. These experiments revealed that within the pulse energy range of 40 to 70 nJ, decreasing pulse energy to 40 nJ did not significantly reduce the spoke wheel marks. More specifically, lenticule cuts were repeated using ex vivo porcine eyes where laser pulse energy was incrementally decreased from 70 nJ to 40 nJ for the anterior incisions, and from 60 nJ to 40 nJ for the posterior incisions. The spoke wheel marks were visible on the residual stromal bed of the ex vivo porcine eyes through the energy range and at the lower-limit laser pulse energy of 40 nJ.

The range of desirable pulse energy is constrained by practical requirements, such as the smoothness of the tissue dissection. For example, below 40 nJ, the laser pulse energy tends to be too close to the plasma threshold of the tissue so the cutting will not be robust. Above 70 nJ, the cavitation bubble tends to be too large to cause roughness in the tissue dissection, which will in turn cause light scattering and reduce visual contrast in the treated eye. Therefore, to obtain high tissue cutting quality, pulse energy should be selected to balance the easiness of lenticule removal (the higher pulse energy, the easier) and the smoothness of the lenticule dissection (the lower pulse energy, the smoother). Generally, pulse energy should be in the range of about 40 nJ to 70 nJ.

Recognizing that it was not desirable to further reduce laser pulse energy in order to eliminate the spoke wheel pattern, further experiments were conducted by changing the scan line step $\Delta$, i.e., changing the sweeping speed. More specifically, lenticule cutting experiments were conducted using ex vivo porcine eyes, where the scan line step $\Delta$ at the edge of the lenticule was increased incrementally in the repeated experiments from 0.8 μm to 2.0 μm, while the scan line step $\Delta$ at the lenticule center was maintained at 2.0 μm, and the $\Delta$ values between the edge and the center were a linear function of the radial distance (distance from the lenticule center). The laser pulse energy was 53 nJ for the anterior lenticule incision and 50 nJ for the posterior lenticule incision, both lower than those used in the clinical trial. The other settings were the same as in the clinical trial. These experiments showed that when the scan line step $\Delta$ at the lenticule edge was below 1.7 μm, the reduction of spoke wheel marks was insignificant. When the scan line step $\Delta$ at the edge was at or above 1.7 μm, significantly reduced presence of the spoke wheel marks was observed. When the scan line step $\Delta$ at the edge was 2.0 μm (represented by curve P3 in FIG. 9A, referred to as the "optimized conditions" in this disclosure), the spoke wheel marks were faint or non-visible, and there were no other surface irregularities such as dimples on the incision surface. This shows that the scan line step was a key factor in the formation and modulation of the noted spoke wheel marks and that increasing scan line step was effective in reducing or eliminating the spoke wheel marks.

Further experiments using live rabbit eyes and ex vivo cadaver eyes also confirmed that when the pulse energy was within the 40 nJ-70 nJ range, and the scan line step $\Delta$ was 2.0 μm at both the lenticule edge and lenticule center, spoke wheel marks were successfully eliminated.

In addition to eliminating spoke wheel marks, the experimental results also demonstrated that under the optimized conditions, the lower value of the energy density and the more even distribution of the energy density across the lenticule surfaces resulted in less bubble generation and accumulation, more uniform bubble distribution, and smoother lenticule and residual stromal bed surfaces. The total amount of the laser energy delivered to the cornea tissue was decreased by 47% under the optimized conditions as compared to the conditions used in the clinical trial. Moreover, the optimized conditions shortened the lenticule incision time from 22-24 seconds under the clinical trial conditions to 14-18 seconds under the optimized conditions.

While in the above experiments the scan line step $\Delta$ was varied as a linear function of the radial distance, the scan line step $\Delta$ may alternatively be a quadratic function, or a higher order polynomial function, or another function of the radial distance. An exemplary quadratic curve with an edge $\Delta$ value of 0.8 μm and a center $\Delta$ value of 2.0 μm is shown as curve P2 in FIG. 9A. In this particular example, there is no constant peripheral ring portion as is the case for the linear curve P1. The quadratic curve provides a greater scan line step and therefore lower energy density at each given radial distance as compared to the linear curve with the same edge and center values. It also results in a faster lenticule cutting procedure and decreases the total amount of laser energy delivered into the cornea tissue during the cutting.

It should be noted that when the scan line step $\Delta$ values are equal at the edge and the center (e.g., both 2.0 μm), the linear and quadratic functions both degenerate into a flat line (such as curve P3 in FIG. 9A).

Figure 9B:
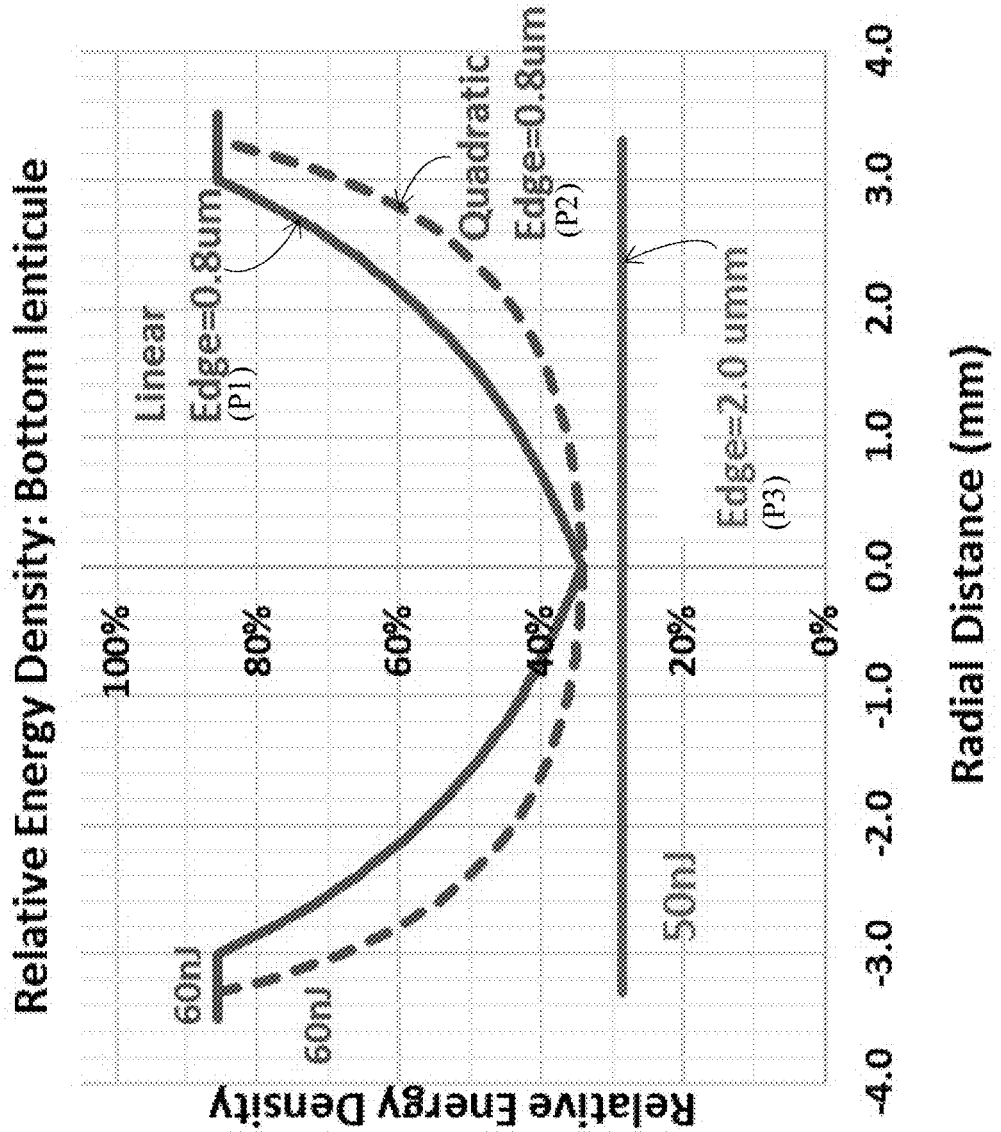
FIG. 9B schematically illustrates the average energy density as a function of radial distance from the lenticule center for the three examples in FIG. 9A.

The calculated average energy density as a function of radial distance for the three examples in FIG. 9A are shown in FIG. 9B. The pulse energy for curves P1 and P2 is 60 nJ (the value used for the posterior lenticule incisions in the clinical trial), and for curve P3 it is 50 nJ (the value used for the posterior lenticule incisions in the ex vivo porcine eye experiments). The average energy densities are shown as a percentage of a reference energy density value, which is calculated using a laser pulse energy of 70 nJ and a scan line step $\Delta$ of 0.8 μm (i.e., the condition for the anterior lenticule edge in the clinical trial). As shown in FIG. 9B, for curve P3, the calculated average energy density is about 29% of the reference value throughout the sweep. For the anterior lenticule incisions in the ex vivo porcine eye experiments (not shown in FIG. 9B), the calculated average energy density is about 30% of the reference value throughout the sweep. For the posterior lenticule incisions under the clinical trial condition (curve P1), the calculated average energy density is between 86% (edges) and 34% (center) of the reference value. For the anterior lenticule incisions under the clinical trial condition (not shown in FIG. 9B), the calculated average energy density is between 100% (edges) and 40% (center) of the reference value.

In further experiments on live rabbit eyes, the scan line step $\Delta$ was increased to 2.1 μm at the lenticule center while the edge scan line step $\Delta$ remained at 2.0 μm, which produced satisfactory results.

More generally, in preferred embodiments, the scan line step $\Delta$ at the center is 2.0 to 2.3 μm. The upper limit of the scan line step is based on multiple considerations. For example, scan line steps higher than 2.3 μm will tend to cause stickiness in the dissection due to insufficient energy density deposited in the tissue. On the other hand, increasing the scan line step at the center may reduce bubble formation and gas accumulation at the center of the lenticular cut area.

In addition to corneal lenticule extraction procedures, the above optimized settings are beneficial for corneal incisions in other procedures, such as a bed cut in a corneal flap. The bed cut is a flat cut, typically having a circular area with a hinge portion, formed by sweeping the laser scan line in a set of parallel sweeps referred to as a raster scan. In a set of experiments, corneal flap incisions were performed on ex vivo porcine eyes under different conditions. When the pulse energy was 65 nJ and scan line step was 0.8 μm, parallel marks near the edges of each sweep (referred to as the lawn-mower-like patterns due to their appearance) were visible on the residual stromal bed of the flap cut. The lawn-mower-like patterns were believed to be formed by similar mechanisms as the spoke-wheel marks in the lenticule incisions. When the pulse energy was 65 nJ but the scan line step was 2.0 μm, there were no lawn-mower-like patterns present on the bed, and also no tissue bridges on the side cut or bed of the flaps. Decreasing the pulse energy to 40 nJ did not eliminate the lawn-mower patterns when the scan line step was 0.8 μm. These observations confirmed the important role of the scan line step in formation of the lawn-mower-type laser-induced marks on the stromal bed surface of the flap cuts. This finding was consistent with the observations on the lenticule incision experiments.

To summarize, embodiments of the present invention provide a method for incising corneal tissue using the fast-scan-slow-sweep laser scanning scheme with optimized settings that eliminate the laser-induced marks near the edges of the sweeps while maintaining tissue bridge-free incisions. The optimized settings use laser pulse energy of 40 nJ-70 nJ and scan line step of 1.7 μm-2.3 μm. The other system parameters for the optimized settings are: The wavelength of the femtosecond laser is 1030 nm, and more generally, 1015 to 1065 nm. The duration of the laser pulse is less than 200 fs at the laser focal spot. The diameter of the laser focal spot in the cornea tissue is 1.3 μm or less. The laser repetition rate is 10 MHz, and more generally, 2 to 40 MHz. The resonant scanner frequency is 7.9 KHz, and more generally, 0.5 to 20 KHz. The number of laser focal spots in each scan line is 50 to 2000. The scan line width is 400 μm to 900 μm, and more generally, 200 μm to 1200 μm. The optimized conditions eliminate spoke wheel marks in the cornea, result in smoother residual bed and lenticular surfaces, and produce more homogenous bubble distribution over the lenticule cut area. When used in corneal lenticule extraction procedures, the method can maintain ease of lenticular extraction and produce rounded and intact lenticule edges.

In some embodiments, the overall lenticular incision procedure is performed in the following steps:
1. Calculate the radius of curvature of the lenticule based on the amount of optical correction, e.g., using Equation (3) for a myopic correction.
2. Select the diameter for the lenticular incision to be extracted.
3. Select laser and optical system parameters, including the laser pulse energy and scan line step parameters described above.
4. Perform bottom surface dissection. In doing so, the fast scan line is preferably kept tangential to the parallels of latitude, and the trajectory of the slow sweep drawn by X, Y, and Z scanning devices moves along the meridians of longitude near south pole in a sequence of 1A to 1B (first sweep of lenticular cut), 2A to 2B (second sweep of lenticular cut), 3A to 3B (third sweep of lenticular cut), and so on, until the full bottom dissection surface is generated.
5. Perform the lenticule side (edge) incision.
6. Perform the top surface dissection in a similar manner as the bottom dissection is done.
7. Perform the entry incision.

Figure 10:
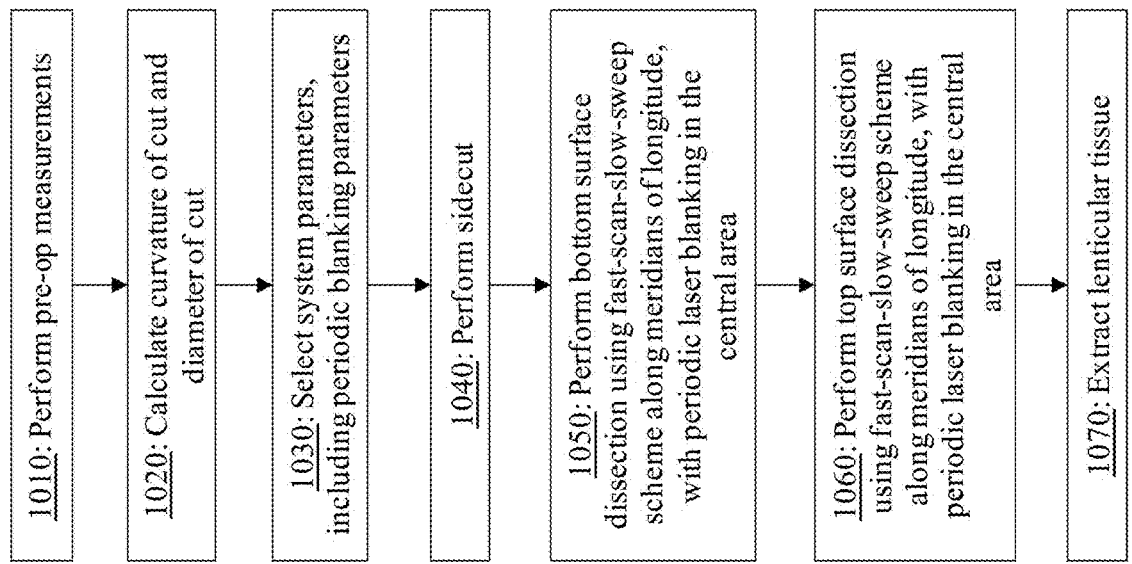
FIG. 10 is a flowchart illustrating a lenticule incision process according to an embodiment of the present invention.

FIG. 10 illustrates a process of the laser system 10 according to an embodiment. The laser system 10 may start a surgical procedure performing pre-operation measurements (Action Block 1010). For example, in an ophthalmologic surgery for myopic correction, the myopic diopter is determined, the reference depth position is determined, and so on. The laser system 10 calculates the radius of curvature based on the amount of correction, e.g., the myopic correction determined in pre-operation measurements, as shown, for example, in equations (2) and (3) above, and calculates the diameter of the incision, as shown by $D_{CUT}$ in FIG. 7 (Action Block 1020). $D_{CUT}$ is equal to or greater than the diameter of the to-be-extracted lenticule (DL in FIG. 7). The system select various laser and optical system parameters, including the pulse energy and scan line step settings (Action Block 1030).

The laser system 10 first performs side incision to provide a vent for gas that can be produced in the lenticular surface dissections, and for tissue extraction later on (Action Block 1040). The laser system 10 then performs the bottom lenticular surface dissection (Action Block 1050) and the top lenticular surface dissection (Action Block 1060). The bottom and top lenticular surface dissection are performed using a fast-scan-slow-sweep scheme along the meridians of longitude, as described above. The lenticular tissue is then extracted (Action Block 1070). Alternatively, the side incision may be performed after the bottom and top lenticular surface dissections.

The above described embodiments solve the problem of redundant energy deposit near the central area by reducing the number of laser pulses delivered in the central area.

All patents and patent applications cited herein are hereby incorporated by reference in their entirety.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

What is claimed is:
1. An ophthalmic surgical laser system comprising:
a laser source configured to generate a pulsed laser beam comprising a plurality of laser pulses;
a laser delivery system configured to deliver the pulsed laser beam to a target tissue in a subject's eye;
a high frequency scanner configured to scan the pulsed laser beam back and forth at a predefined frequency;
an XY-scanner configured to deflect the pulsed laser beam, the XY-scanner being separate from the high frequency scanner;
a Z-scanner configured to modify a depth of a focus of the pulsed laser beam; and
a controller configured to control the laser source, the high frequency scanner, the XY-scanner and the Z-scanner to successively form a plurality of sweeps which collectively form at least one lenticular incision of a lens in the subject's eye, the lens having a curved surface that defines an apex and a Z axis passing through the apex, wherein each sweep is formed by:
controlling the laser source to generate the pulsed laser beam having a pulse energy of 40 nJ to 70 nJ;
controlling the high frequency scanner to deflect the pulsed laser beam to form a scan line, the scan line being a straight line having a predefined length and being tangential to a parallel of latitude of the lens, the parallel of latitude being a circle on the surface of the lens that is perpendicular to the Z axis and has a defined distance to the apex, and controlling the XY-scanner and the Z-scanner to move the scan line along a meridian of longitude of the lens, the meridian of longitude being a curve that passes through the apex and has a defined angular position around the Z axis, wherein the scan line is moved at a sweeping speed that produces a scan line step of between 1.7 µm and 2.3 µm, the scan line step being a distance between a center of consecutive scan lines;

wherein the plurality of sweeps are successively formed one after another along the respective meridians of longitude which are different from one another.

2. The ophthalmic surgical laser system of claim 1, wherein the scan line step is between 1.7 µm and 2.0 µm at an edge of the lenticular incision and between 2.0 µm and 2.3 µm at a center of the lenticular incision.

3. The ophthalmic surgical laser system of claim 1, wherein the scan line step is a constant throughout each sweep.

4. The ophthalmic surgical laser system of claim 1, wherein the scan line step is a linear function of a radial distance from the center of the lenticular incision within a predefined radial distance.

5. The ophthalmic surgical laser system of claim 1, wherein the scan line step is a quadratic or higher order polynomial function of a radial distance from the center of the lenticular incision within a predefined radial distance.

6. The ophthalmic surgical laser system of claim 1, wherein the pulsed laser beam has a repetition rate of 2 to 40 MHz, wherein the high frequency scanner is a resonant scanner with a scanning frequency of 0.5 kHz and 20 kHz, and wherein the predetermined length of the scan lines is between 200 µm and 1200 µm.

7. The ophthalmic surgical laser system of claim 1, wherein the pulsed laser beam has a wavelength of 1015 to 1065 nm, a pulse duration of less than 200 fs, and a laser focal spot diameter in the target tissue of 1.3 µm or less.

8. The ophthalmic surgical laser system of claim 1, further comprising a prism disposed to receive scanned pulsed laser beam from the high frequency scanner, and wherein the controller is configured to rotate the prism to rotate an orientation of the scan line between successive sweeps.

9. The ophthalmic surgical laser system of claim 1, wherein the at least one lenticular incision includes a top lenticular incision and a bottom lenticular incision, wherein the curved surface is a top surface of the lens corresponding to the top lenticular incision, the lens further including a bottom surface corresponding to the bottom lenticular incision and defining another apex, and wherein the scan line for each of the sweeps forming the top lenticular incision is moved over the top surface of the lens through the apex of the top surface of the lens, and the scan line for each of the sweeps forming the bottom lenticular incision is moved over the bottom surface of the lens through the other apex of the bottom surface of the lens.

10. A method for creating a lenticular incision using an ophthalmic surgical laser system, the method comprising the steps of:

generating, by a laser source, a pulsed laser beam comprising a plurality of laser pulses;

delivering, by a laser delivery system, the pulsed laser beam to a target tissue in a subject's eye;

scanning, by a high frequency scanner, the pulsed laser beam back and forth at a predefined frequency;

deflecting, by an XY-scanner, the pulsed laser beam, the XY-scanner being separate from the high frequency scanner;

modifying, by a Z-scanner, a depth of a focus of the pulsed laser beam; and controlling, by a controller, the laser source, the high frequency scanner, the XY-scanner and the Z-scanner to successively form a plurality of sweeps which collectively form at least one lenticular incision of a lens in the subject's eye, the lens having a curved surface that defines an apex and a Z axis passing through the apex, including forming each sweep by:

controlling the laser source to generate the pulsed laser beam having a pulse energy of 40 nJ to 70 nJ;

controlling the high frequency scanner to deflect the pulsed laser beam to form a scan line, the scan line being a straight line having a predefined length and being tangential to a parallel of latitude of the lens, the parallel of latitude being a circle on the surface of the lens that is perpendicular to the Z axis and has a defined distance to the apex, and controlling the XY-scanner and the Z-scanner to move the scan line along a meridian of longitude of the lens, the meridian of longitude being a curve that passes through the apex and has a defined angular position around the Z axis, wherein the scan line is moved at a sweeping speed that produces a scan line step of between 1.7 µm and 2.3 µm, the scan line step being a distance between a center of consecutive scan lines;

wherein the plurality of sweeps are successively formed one after another along the respective meridians of longitude which are different from one another.

11. The method of claim 10, wherein the scan line step is between 1.7 µm and 2.0 µm at an edge of the lenticular incision and between 2.0 µm and 2.3 µm at a center of the lenticular incision.

12. The method of claim 10, wherein the scan line step is a constant throughout each sweep.

13. The method of claim 10, wherein the scan line step is a linear function of a radial distance from the center of the lenticular incision within a predefined radial distance.

14. The method of claim 10, wherein the scan line step is a quadratic or higher order polynomial function of a radial distance from the center of the lenticular incision within a predefined radial distance.

15. The method of claim 10, wherein the pulsed laser beam has a repetition rate of 2 to 40 MHz, wherein the high frequency scanner is a resonant scanner with a scanning frequency of 0.5 kHz and 20 kHz, and wherein the predetermined length of the scan lines is between 200 µm and 1200 µm.

16. The method of claim 10, wherein the pulsed laser beam has a wavelength of 1015 to 1065 nm, a pulse duration of less than 200 fs, and a laser focal spot diameter in the target tissue of 1.3 µm or less.

17. The method of claim 10, further comprising, by a prism disposed to receive scanned pulsed laser beam from the high frequency scanner, rotating an orientation of the scan line between successive sweeps.

18. The method of claim 10, wherein the at least one lenticular incision includes a top lenticular incision and a bottom lenticular incision, wherein the curved surface is a top surface of the lens corresponding to the top lenticular incision, the lens further including a bottom surface corresponding to the bottom lenticular incision and defining another apex, and wherein the scan line for each of the sweeps forming the top lenticular incision is moved over the top surface of the lens through the apex of the top surface of the lens, and the scan line for each of the sweeps forming the bottom lenticular incision is moved over the bottom surface of the lens through the other apex of the bottom surface of the lens.

19. An ophthalmic surgical laser system comprising:
- a laser source configured to generate a pulsed laser beam comprising a plurality of laser pulses;
- a laser delivery system configured to deliver the pulsed laser beam to a target tissue in a subject's eye;
- a high frequency scanner configured to scan the pulsed laser beam back and forth at a predefined frequency;
- an XY-scanner configured to deflect the pulsed laser beam, the XY-scanner being separate from the high frequency scanner;
- a Z-scanner configured to modify a depth of a focus of the pulsed laser beam; and
- a controller configured to control the laser source, the high frequency scanner, the XY-scanner and the Z-scanner to successively form a plurality of sweeps which collectively form a bed cut in the target tissue, wherein each sweep is formed by:
  - controlling the laser source to generate the pulsed laser beam having a pulse energy of 40 nJ to 70 nJ;
  - controlling the high frequency scanner to deflect the pulsed laser beam to form a scan line, the scan line being a straight line having a predefined length, and
  - controlling the XY-scanner to move the scan line along a predetermined direction, wherein the scan line is moved at a sweeping speed that produces a scan line step of between 1.7 µm and 2.3 µm, the scan line step being a distance between a center of consecutive scan lines.

20. The ophthalmic surgical laser system of claim 19, wherein the scan line step is a constant throughout each sweep.

* * * * *